United States Patent [19]

Alderman

[11] Patent Number: 4,704,285

[45] Date of Patent: Nov. 3, 1987

[54] SUSTAINED RELEASE COMPOSITIONS COMPRISING HYDROXYPROPYL CELLULOSE ETHERS

[75] Inventor: Daniel A. Alderman, Midland, Mich.

[73] Assignee: The Dow Chemical Company, Midland, Mich.

[21] Appl. No.: 799,044

[22] Filed: Nov. 18, 1985

[51] Int. Cl.$^4$ .................. A61K 9/02; A61K 9/20; A61K 9/22; A61K 9/26

[52] U.S. Cl. .................. 424/468; 424/465; 424/480; 514/781; 514/965

[58] Field of Search .............. 424/19, 22, 465, 468, 424/480; 514/781, 965

[56] References Cited

U.S. PATENT DOCUMENTS

| | | | |
|---|---|---|---|
| 3,951,821 | 4/1976 | Davidson | 514/781 |
| 4,107,288 | 8/1978 | Oppenheim et al. | 424/22 |
| 4,269,859 | 5/1981 | Morse | 514/781 |
| 4,369,172 | 1/1983 | Schor et al. | 514/781 |

FOREIGN PATENT DOCUMENTS

| | | | |
|---|---|---|---|
| 2050701 | 5/1971 | Fed. Rep. of Germany | 514/781 |
| 2518270 | 3/1976 | Fed. Rep. of Germany | 514/781 |
| 56-57719 | 5/1981 | Japan | 514/781 |
| 59-193815 | 11/1984 | Japan | 514/781 |
| 1405088 | 9/1975 | United Kingdom | 514/781 |

OTHER PUBLICATIONS

Machida et al., *Directly Compressed Tablets Containing Hydroxy-Propyl Cellulose in Addition to Starch or Lactose*, Chem. Pharm. Bull. 22(10) 2346–2351 (1974).

*Primary Examiner*—Ronald W. Griffin
*Attorney, Agent, or Firm*—Stephen S. Grace

[57] ABSTRACT

Solid tablets of a therapeutically active composition exhibit sustained release properties when compressed with a fine particle sized hydroxypropyl cellulose ether composition.

9 Claims, No Drawings

SUSTAINED RELEASE COMPOSITIONS COMPRISING HYDROXYPROPYL CELLULOSE ETHERS

BACKGROUND OF THE INVENTION

This invention relates to sustained release tablets, and particularly to such tablets comprised of a fine particle sized hydrophilic polymeric composition.

Polymeric compositions have been widely used as a matrix base for compressed tablets. Such tablets typically contain a medicament or a vitamin whose rate of release upon administration is delayed or controlled by the matrix base. Controlled release tablets are desirable because they provide a method of delivering a long-lasting dose in a single application without overdosing the patient.

Typically, an effective amount of the polymeric matrix composition is employed. It is desirable to employ as little amount of polymeric composition as possible to provide the intended release profile, to obtain minimum dosage size or to obtain good compression properties. For such applications, a highly hydrophilic polymeric composition is suitably employed. Such a composition rapidly hydrates and forms a gel-like layer in the tablet through which the dosage composition is released to the system. An example of a preferred hydrophilic polymeric composition is a cellulose ether sold as METHOCEL® K4M and K15M by The Dow Chemical Company, which has a hydropropoxyl substitution of between about 4 to about 12 weight percent, and a methoxyl substitution of between about 19 to about 25 weight percent.

In U.S. Pat. No. 4,369,172 it is disclosed that hydroxypropyl methylcellulose ethers having a hydroxypropoxyl content of from 9 to 12 percent and a number average molecular weight of less than about 50,000 provides the best sustained release. Rather than the effect of hydration and gel formation, the chemical composition of the hydroxypropyl methylcellulose is emphasized.

Cellulose ethers, such as METHOCEL® K, are desirable polymeric matrix compositions because they are derived from naturally occurring cellulose, and are free-flowing, readily compressible powders. Unfortunately, not all cellulose ethers hydrate rapidly, and therefore do not provide a desirable release profile for compressed tablets. For example, hydroxypropyl cellulose is commercially available in granular form. Such granules are not suitable for compressing tablets and do not hydrate rapidly.

Yet another factor affecting the performance of the tablet is the chemical characteristics of the drug employed. Certain polymers can be employed beneficially for some drugs, but not for others. The degree of water-solubility of the drug, the drug's molecular weight and the diffusion coefficient in a hydrated polymer gel layer can be critical.

It would be desirable to have additional cellulose ether polymeric matrix materials which would provide sufficient release profiles for compressed tablets.

SUMMARY OF THE INVENTION

This invention is a sustained release, compressed solid tablet of a therapeutically active composition. The tablet comprises a functionally effective amount of fine particle sized hydroxypropyl cellulose ether composition. The hydroxypropyl cellulose ether composition is in the form of a powder and is sufficiently fine that the release of active composition from the solid tablet is delayed longer upon contacting an aqueous acidic environment at 37° C., compared to a tablet formulated with a chemically identical but coarser particle sized hydroxypropyl cellulose ether composition.

In another aspect, this invention is a process for providing sustained release solid tablets of a therapeutically active composition. The process comprises intimately mixing an amount of the active composition in the form of a powder with a functionally effective amount of a fine particle sized hydroxypropyl cellulose ether composition. The cellulose ether composition is in the form of a powder and the intimate mixture is subjected to compression conditions to form a solid tablet. The cellulose ether composition is sufficiently fine that the release of active composition from the solid tablet is delayed longer upon contacting an aqueous acidic environment at 37° C.; compared to a tablet formulated with a chemically identical but coarser particle sized hydroxypropyl cellulose ether composition.

This invention is useful in providing compressed solid tablets of a therapeutically active composition and cellulose ether composition which exhibit sustained release of the active composition.

DETAILED DESCRIPTION OF THE INVENTION

The hydroxypropyl cellulose ether composition (HPC) of this invention has a hydroxypropoxyl substitution sufficient to render the polymer water-soluble. Such amount can vary and typically ranges from about 20 to about 80 weight percent, and preferably from about 40 to about 80 weight percent, as described in the National Formulary. Such cellulose ethers can be prepared by reacting propylene oxide with alkali cellulose. Hydroxypropyl cellulose ether is readily commercially available from Hercules under the trade name KLUCEL®, and NISSO HPC® from Nippon Soda.

The HPC of this invention is in the form of a powder and has a particle size sufficiently fine that the release of active composition from a solid tablet is delayed longer upon contacting an aqueous acidic environment at 37° C.; compared to a tablet formulated with a chemically identical but coarser particle sized HPC. Typically, such particle size is sufficient when the HPC hydrates rapidly, forming a gel-like layer, upon contacting an aqueous environment. Such particle size can vary and typically is sufficient when at least 50 weight percent of the particles can pass through a 100 mesh screen, and preferably when at least 70 weight percent can pass through a 100 mesh screen, although any particle size which exhibits comparative sustained release can be employed.

A cellulose ether composition is chemically identical, for purposes of this invention, when it possesses hydroxypropoxyl substitution as defined as HPC NF grade and has a 2 percent aqueous solution viscosity within about 50 percent of the viscosity of the fine particle sized composition. A cellulose ether composition is coarse when the particle size distribution has a larger amount by weight of larger particles than the fine particle sized cellulose ether composition.

The cellulose ether composition is substantially water-soluble. Substantially water-soluble refers to a composition which tends to spontaneously disperse its molecules throughout the molecules of water.

A functionally effective amount of the cellulose ether composition is employed. Such amount is an amount sufficient to delay the release of the therapeutically active composition. Preferably, the amount employed is the minimum amount required to provide the delayed release. Such an amount can vary and typically ranges from about 5 to about 90 percent, preferably from about 5 to about 25 percent, and most preferably from about 10 to about 17 percent based on weight of the tablet, although any functionally effective amount can be employed.

The therapeutically active composition is any composition which can be administered orally to affect a condition such as, for example, a pharmaceutical drug or vitamin. The active composition can be a water-soluble or a water-insoluble composition. A water-soluble composition is a composition which spontaneously disperses its molecules in an aqueous medium, and a water-insoluble composition is a composition which does not exhibit that spontaneous dispersion. Suitable water-soluble compositions include aspirin, theophylline, pseudoephedrine HCl, ascorbic acid, riboflavin, 5 phosphate sodium and the like. Suitable water-insoluble compositions include naproxyn and ibuprofen. Water-soluble compositions especially find the process of the invention useful because they tend to dissolve and diffuse through the hydrated cellulose ether layer during gel formation.

The therapeutically active composition is employed in any effective dosage amount. Such amount is an amount sufficient to affect the condition to be treated. The amount can vary according to the specific active composition employed, and such variations are within the knowledge of the skilled artisan. Typically, the active composition can be employed up to about 95 weight percent of the compressed tablet, although any effective weight percent can be employed.

An additional hydrophilic colloid can be employed in conjunction with the HPC of this invention. Suitable hydrophilic colloids are water-soluble cellulose ethers, such as hydroxypropyl methylcellulose (HPMC). It is not critical that such optional hydrophilic colloids be fine particle sized compositions, although for certain active compositions it can be desirable. For such compositions, it is desirable that the HPMC have a particle size sufficient that at least 70 weight percent can pass through a 100 mesh screen and preferable at least 70 weight percent can pass through a −140 mesh screen. The HPMC's which are designated as HPMC 2208 USP and HPMC 2910 are preferred. Such HPMC's have a hydroxypropoxyl content of between about 4 and 12 weight percent and a methoxyl content of between about 19 and 30 weight percent. The HPMC's can exhibit a 2 percent aqueous solution viscosity of between about 100 and 100,000 cps, and are readily commercially available from The Dow Chemical Company under the trade name METHOCEL ®.

The optional HPMC can be employed in any functionally effective amount. Such amount can vary, and typically ranges from about 5 to about 75 weight percent of polymer mixture, and up to about 90 weight percent of the tablet in combination with the HPC. Preferably, the HPC is employed in greater than about 30 weight percent based on the combined weight percent of HPMC and HPC, because the flow properties and thereby the compression properties are improved.

Typically, tablets can contain one or more optional compositions or excipients such as diluents or fillers, binders, lubricants and glidants. Diluents or fillers are compositions which can provide bulk and binding properties. Examples of suitable diluents or fillers are lactose, mannitol and the like. Typically, such diluents or fillers can be employed in the formulation up to about 80 weight percent, and preferably up to about 60 weight percent. Binders are compositions which can bind the components of the tablets together and are typically employed in a wet granulation process. Examples of suitable binders are starch and polyvinylpyrrolidinone. Typically, such binders are employed in from about 3 to about 8 weight percent. Lubricants are compositions which can prevent sticking to die walls or punch faces. Examples of suitable lubricants are magnesium stearate, stearic acid and the like. Typically, such lubricants are employed in an amount from about 0.5 to 3.0 weight percent. Glidants are compositions which can aid powder flow. An example of a suitable glidant is fumed silica. Typically, such glidants are employed in an amount from about 0.1 to 3.0 weight percent.

The active composition, polymer and optional ingredients are uniformly mixed together in powder form to provide a homogeneous mixture. The mixture is then subjected to compression to provide a solid tablet. Before compressing, the mixture can be subjected to a wet or dry granulation process. The powder or granulated mixture is fed to the die of a tablet press and sufficient pressure is applied to form a solid tablet. Such pressure can vary, and typically ranges from about 1,000 psi to about 6,000 psi, and preferably about 2,000 psi force. A solid tablet can substantially retain its form under conventional storage and handling conditions. The tablet also maintains its solid form upon administration, and provides sustained release of the active composition through diffusion and erosion.

Advantageously, the mixture of tablet ingredients can be treated in a dry granulation process or a wet granulation process. In a dry granulation process, the mixture is precompressed and milled into the desired size prior to tableting. In a wet granulation process, the mixture is combined and formed into granules with a polymeric binder solution and then sized and/or dried at the desired particle size prior to tableting. The size of the granulated mixture is not critical to the drug release rate. The release rate is affected, according to this invention, by the particle size of the cellulose ether composition prior to granulating.

The tablets are suitable for administering a therapeutically active composition to humans. Upon contacting the aqueous acidic environment typically present in humans, the tablets slowly dissolve. Typically, the acidic environment is provided by gastric juices, and is at about 37° C.

Solid tablets formulated with the small particle sized cellulose ether composition of this invention surprisingly have a longer release profile compared to tablets formulated with a chemically identical cellulose ether composition which has a larger particle size distribution. When the cellulose ether composition has a particle size sufficiently small that at least about 50 weight percent can pass through a 100 mesh screen, the tablets typically require at least one hour, preferably at least two hours, and more preferably at least four hours longer to release the active composition compared to tablets formulated with a chemically identical cellulose ether composition having a particle size in which less than 50 weight percent can pass through a 100 mesh screen.

The following examples are illustrative only, and are not intended to limit the scope of the invention.

EXAMPLE 1

The particle size distributions of two samples of HPC are measured and the results are provided in Table A.

TABLE A

| Sieve Size | Weight Percent Retained | |
|---|---|---|
| | HPC #1 | HPC C-1* |
| 60 | 28.19 | 56.85 |
| 80 | 12.09 | 15.93 |
| 100 | 9.26 | 6.06 |
| 140 | 3.92 | 8.80 |
| 200 | 4.67 | 5.31 |
| 325 | 31.36 | 4.81 |
| Pan | 10.51 | 2.24 |

*Not an example of this invention.

A tablet is formulated using the samples of HPC of Table A. The formulation is:
68.3 percent latose Fast Flo ® (Foremost McKesson)
16.0 percent pseudoephedrine, HCl
15 percent HPC polymer
0.7 percent magnesium stearate.
The tablets are 750 mg, and are compressed at 3,000 psi in a ½ inch standard concave punch. The tablets are dissolved in a USP paddle dissolution device at 100 rpm in a 0.1N HCl solution at 37° C. The percent dissolved over time is provided in Table B.

TABLE B

| Time (Hours) | Percent Dissolved[1] | |
|---|---|---|
| | HPC #1 | HPC C-1* |
| 0 | 0 | 0 |
| 0.5 | 21 | 44 |
| 1.5 | 44 | 96 |
| 3.0 | 64 | 100 |
| 5.0 | 81 | |
| 7.0 | 94 | |
| 9.0 | 98 | |
| 11.0 | 99 | |

*Not an example of the invention.
[1]Percent of pseudoephedrine, HCl dissolved into solution.

This example illustrates the delayed release effect a fine particle sized (at least 50 weight percent passing through −100 mesh screen, HPC #1) HPC provides an active composition versus the release of a coarse particle sized HPC (HPC C-1).

EXAMPLE 2

Tablets are prepared employing the HPC's of Example 1 in combination with HPMC 2910 and HPMC 2208. The tablet formulation is:
78 percent lactose, sray dried
9 percent HPMC
6 percent HPC
5 percent riboflavin
2 percent stearic acid.
The tablets are 1,000 mg and are compressed at 3,000 psi in a ½ inch standard concave punch. The dissolution rates of the tablets are measured according to the method of Example 1 and the results are provided in the following table.

| Time (Hours) | Percent Dissolved | | | HPMC[3]/HPC |
|---|---|---|---|---|
| | HPMC 2910[2]/HPC-1 | HPMC 2910[2]/HPC C-1* | HPMC 2208[3]/HPC-1 | 2208 C-1* |
| 0 | 0 | 0 | 0 | 0 |
| 0.5 | 24.6 | 25.8 | 12.7 | 21 |
| 1.5 | 35.8 | 36.4 | 19.3 | 26.4 |
| 3.0 | 46.8 | 44.7 | 26.8 | 39.1 |
| 5.0 | 60.8 | 95.7 | 36.6 | 54.6 |
| 7.0 | 85.8 | 100 | 47.2 | 68.6 |
| 9.0 | Stopped Test | — | 58.2 | Stopped Test |
| 11.0 | | | 97.9 | |
| 13.0 | | | 100 | |

*Not an example of this invention.
[2]Has a hydroxyproxyl content of between 7 and 12 weight percent, a methoxyl content of between 28 and 30 weight percent, and a 2 percent aqueous solution viscosity of about 4,000 cps.
[3]Has a hydroxypropoxyl content of between about 4 and 12 weight percent, a methoxyl content of between about 9 and 25 weight percent, and a 2 percent aqueous solution viscosity of about 4,000 cps.

This example illustrates the advantages fine particle sized HPC provides to known sustained release polymers.

EXAMPLE 3

A course particle sized HPC is ball milled to a finer particle size, and is compared to a coarse HPC in the following table.

| Seive Size | Weight Percent Retained | |
|---|---|---|
| | HPC-2 (Fine) | HPC C-2* (Coarse) |
| 60 | 20.1 | 76.3 |
| 80 | 15.6 | 9.2 |
| 100 | 11.5 | 3.1 |
| 140 | 30.5 | 4.5 |
| 200 | 2.9 | 0.2 |
| <200 | 19.6 | 5.1 |

*Not an example of this invention.

Tablets are prepared according to the following formulation:
56.67 percent lactose
16 percent pseudoephedrine, HCl
26.67 percent HPC
10.67 percent magnesium stearate.
Three tablets are prepared, one using HPC C-2*, one using the −100 to −140 mesh fraction of HPC-2, and one using the <−200 mesh fraction of HPC-2.

The dissolution rates of the tablets are measured according to the method of Example 1 and the results are provided in the following Table:

| Time (Hours) | HPC-2 (−100 to −140 mesh) | Percent Dissolved HPC-2 (<−200 mesh) | HPC C-2* |
|---|---|---|---|
| 0 | 0 | 0 | 0 |
| 0.5 | 25.17 | 23.4 | 46.47 |
| 1.5 | 42.7 | 44.53 | 90.34 |
| 3.0 | 61.1 | 63.96 | 97.7 |
| 5.0 | 76.5 | 81.73 | 100 |
| 7.0 | 88.2 | 91.7 | |
| 9.0 | 94.7 | 97.3 | |

| Time (Hours) | HPC-2 (−100 to −140 mesh) | Percent Dissolved HPC-2 (<−200 mesh) | HPC C-2* |
|---|---|---|---|
| 11.0 | 98.7 | 100 | |
| 13.0 | 100 | — | |

*Not an example of this invention.

What is claimed is:

1. A sustained release solid tablet of a therapeutically active composition, the tablet comprising a functionally effective amount of a fine particle sized hydroxypropyl cellulose ether composition in the form of a powder, wherein the cellulose ether composition is (a) water soluble and (b) is sufficiently fine that (i) at least 50 weight percent of the particles of the cellulose ether composition can pass through a 100 mesh screen and (ii) the release of the active composition from the solid tablet is delayed longer upon contacting an aqueous acidic environment at 37° C., compared to a tablet formulated with a chemically identical but coarser particle sized hydroxypropyl cellulose ether composition.

2. The tablet of claim 1, further comprising a functionally effective amount of a filler composition.

3. The tablet of claim 2, further comprising a functionally effective amount of a lubricant composition.

4. The tablet of claim 1, further comprising a hydroxypropyl methylcellulose ether composition.

5. The tablet of claim 4, wherein the hydroxypropyl methylcellulose ether composition has a hydroxypropoxyl content of between about 4 and about 12 weight percent, a methoxyl content of between about 19 and about 30 weight percent, and a 2 percent aqueous solution viscosity of between about 400 and 100,000 cps.

6. The tablet of claim 5, wherein at least 50 weight percent of the particles of the hydroxypropyl cellulose ether composition can pass through a 100 mesh screen.

7. The tablet of claim 5, wherein the hydroxypropyl cellulose ether composition comprises at least about 30 weight percent of the combined weight of hydroxypropyl cellulose ether composition and hydroxypropyl methylcellulose ether composition.

8. The tablet of claim 7, wherein at least 50 weight percent of the particles of the hydroxypropyl cellulose ether composition can pass through a 100 mesh screen, and at least 70 weight percent of the hydroxypropyl methylcellulose ether composition can pass through a 100 mesh screen.

9. The tablet of claim 8, wherein at least 50 weight percent of the particles of the hydroxypropyl cellulose ether composition can pass through a 100 mesh screen, and at least 70 weight percent of the hydroxypropyl methylcellulose ether composition can pass through a 140 mesh screen.

* * * * *